United States Patent [19]

Kubicek

[11] 4,005,149

[45] Jan. 25, 1977

[54] MERCAPTANS BY HYDROGEN SULFIDE-CLEAVAGE OF ORGANIC SULFIDES IN PRESENCE OF CARBON DISULFIDE

[75] Inventor: Donald H. Kubicek, Bartlesville, Okla.

[73] Assignee: Phillips Petroleum Company, Bartlesville, Okla.

[22] Filed: May 1, 1975

[21] Appl. No.: 573,486

[52] U.S. Cl. .................. 260/609 R; 260/609 D
[51] Int. Cl.² ............................... C07C 148/00
[58] Field of Search ........................... 260/609 R

[56] References Cited

UNITED STATES PATENTS

| | | | |
|---|---|---|---|
| 2,667,515 | 1/1954 | Beach | 260/609 R |
| 2,829,171 | 4/1958 | Doumani | 260/609 R |
| 3,069,472 | 12/1962 | Loev | 260/609 R |
| 3,081,353 | 3/1963 | Forni | 260/609 R |
| 3,488,739 | 1/1970 | Venrooy | 260/609 R |
| 3,880,933 | 4/1975 | Kubicek | 260/609 R |

*Primary Examiner*—Lewis Gotts
*Assistant Examiner*—D. R. Phillips

[57] ABSTRACT

In a process for preparing mercaptans by catalytic cleavage of organic sulfides with hydrogen sulfide in the presence of sulfactive catalysts a method is provided for increasing the total conversion of reactants to mercaptans by including carbon disulfide in the reaction mixture. In a preferred embodiment carbon disulfide is present in the reaction mixture of hydrogen sulfide and organic sulfides in an amount in the molar ratio of about 0.1/1 to about 50/1 organic sulfide to carbon disulfide.

5 Claims, No Drawings

MERCAPTANS BY HYDROGEN SULFIDE-CLEAVAGE OF ORGANIC SULFIDES IN PRESENCE OF CARBON DISULFIDE

BACKGROUND OF THE INVENTION

This invention pertains to the preparation of mercaptans. In a more specific aspect of this invention it pertains to the preparation of mercaptans by the cleavage reaction of organic sulfides with hydrogen sulfide. In another aspect of this invention it pertains to an improvement in the conversion of reactants in the process of preparing mercaptans from the cleavage reaction of organic sulfides with hydrogen sulfide in the presence of a sulfactive catalyst.

It is well known in the art to prepare mercaptans by the cleavage of organic sulfides with hydrogen sulfide in the presence of a sulfactive catalyst. This reaction has been modified by the use of various promoters for the catalyst and by the presence of modifying compounds along with the reactants. I have discovered that the presence of carbon disulfide in the reaction mixture enhances the conversion of reactants to the desired mercaptan products.

It is, therefore, an object of this invention to provide a method for improving the conversion to mercaptans product in the cleavage of organic sulfides with hydrogen sulfide.

Other aspects, objects and the various advantages of this invention will become apparent upon reading of the specification and the appended claims.

STATEMENT OF THE INVENTION

According to the present invention, in the preparation of mercaptans by cleavage of organic sulfides with hydrogen sulfide in the presence of a sulfactive catalyst a method for increasing the total conversion of reactants to mercaptans is provided by adding carbon disulfide to the reaction mixture.

The organic sulfides useful in the practice of this invention include those of general formula R—S—R; wherein the R groups are independently selected from the group consisting of alkyl, cycloalkyl and aryl radicals and combination radicals such as alkylcycloalkyl, aralkyl, alkaryl and the like; wherein the R groups are selected such that the useful sulfides generally contain from 2 to about 40 or more carbon atoms per molecule with a preferable range of carbon atoms being from 2 to about 16.

Examples of useful sulfides include dimethyl sulfide, diethyl sulfide, diisopropyl sulfide, di-n-butyl sulfide, di-n-octyl sulfide, di-n-dodecyl sulfide, di-n-eicosyl sulfide, methyl ethyl sulfide, n-pentyl-n-heptyl sulfide, dicyclohexyl sulfide, bis(4-methylcyclohexyl sulfide, diphenyl sulfide, di-p-tolyl sulfide, bis(p-n-hexylphenyl) sulfide, dibenzyl sulfide, and the like. Mixtures of sulfides as feedstock as well as mixtures of sulfide with other inert components are within the scope of this invention.

Catalysts, which are generally useful in the conversion of sulfides to mercaptans, are those described as sulfactive hydrogenation catalysts, including sulfides of Group VI or Group VIII metals, either alone or in combination. For example, the sulfides of cobalt, nickel, molybdenum, iron, tungsten, chromium, platinum, etc., are useful. The catalytic material is usually deposited on such well-known supports as activated carbon, alumina, zirconia, silica, thoria, pumice, and silica-alumina compositions. Cobalt-molybdenum catalysts supported on alumina are generally preferred. Quite effective catalysts of the foregoing description, but in the oxide form, are commercially available. These catalysts in the oxide form can be pre-sulfided using well-known sulfiding techniques or can be used directly without prior sulfiding since, under the hereinafter described reaction conditions, sulfiding occurs rapidly. An especially preferred commercially available catalyst contains 3 to 4 weight percent cobalt oxide and 15 to 16 weight percent molybdenum oxide with the remainder being alumina and is commonly referred to as cobalt molybdate on alumina.

Hydrogen sulfide is employed in this invention in amounts sufficient to give the desired degree of cleavage of the organic sulfide feedstock. Hydrogen sulfide/organic sulfide mole ratios generally in the range of about 1/1 to about 40/1 and preferably about 1.5/1 to about 30/1 are employed.

The use of any amount of carbon disulfide will affect the reaction so that carbon disulfide is employed in this invention in an amount sufficient to produce the desired effect on the reaction. Generally organic sulfide/carbon disulfide mole ratios in the range about 0.1/1 to about 50/1 and preferably about .25/1 to about 10/1 produce the desired results.

If desired, an inert diluent can be employed in the feedstream to dilute or fluidize the feedstream. Such diluents may be especially desirable with higher molecular-weight organic sulfide to facilitate flow to and from the reactor. Such diluents include hydrocarbons such as pentane, hexane, benzene, toluene, xylenes, etc. They can be used in any suitable amounts.

The above-described ingredients of the feedstream are intimately mixed by any means well known in the prior art and are then contacted with the catalyst in any suitable reaction zone under any suitable sulfide-cleaving conditions which produce the desired results. This invention is especially well suited for use of a continuous reactor, but, if desired, a batch reactor can be employed.

Reaction temperatures can vary widely depending on other reaction conditions, as well as, on reactivity of the sulfide feedstock and on degree of sulfide cleavage desired. Generally temperatures in the range of about 350° to about 700° F (177° to 371° C) can be employed to produce the desired results, though it is preferable because of rate, side-reactions, etc., to employ temperatures in the range of about 450° to about 600° F (232° – 315° C).

Reaction pressures can vary widely. Usually pressures in the range of about 100 to about 5000 psig can be used, though, as a matter of convenience, pressures of about 150 to about 750 psig are normally preferred.

Contact time of reactants with catalyst under suitable sulfide-cleaving conditions can vary widely depending on reactivity of organic sulfide, desired degree of sulfide-cleavage, other reaction conditions, etc. However, weight hourly space velocities (weight feed/weight catalyst/hour) in the range of 0.1 to 10 preferably 0.4 to 2 are normally employed.

EXAMPLE

A conventional stainless steel tubular reactor ½ inch diameter and 18 inches long fitted with a ¼ inch diameter internal thermocouple well extending the length of the reactor was utilized in the working example. The catalyst employed was cobalt molybdate on alumina.

The catalyst (50 gm, about 75 cc) was sulfided by contact with hydrogen sulfide for 4 hours at 600° F (315° C) before contact with feed. The reactor was electrically heated. A gas chromatograph was employed for product analysis.

Comparative runs (odd numbered runs 1 to 23) and inventive runs (even numbered runs 2 to 24) were conducted in the above-described reactor employing feed and reaction conditions described in Table I. Results are tabulated in Table II.

TABLE I

| Run No.[a] | Press. Psig | Organic Sulfide | $H_2S/R_2S$ Mole/Hr | $R_2S/CS_2$ Mole/Hr |
|---|---|---|---|---|
| 1,3,5,7 | 450 | Dimethyl | 1.14/0.57 | — |
| 2,4,6,8 | 450 | Dimethyl | 1.14/0.57 | 0.57/0.08 |
| 9,11,13,15,17 | 450 | Di-n-butyl | 2.0/0.5 | — |
| 10,12,14,16,18 | 450 | Di-n-butyl | 1.96/0.49 | 0.49/0.08 |
| 19,21,23 | 450 | Di-n-octyl[b] | 2.4/0.24[c] | — |
| 20,22,24 | 450 | Di-n-octyl[b] | 2.3/0.23[c] | 0.23/0.10 |

[a]Odd numbers - comparative runs; even numbers - inventive runs.
[b]Mixture containing 43% di-n-octyl sulfide and 57% di-n-octyl disulfide.
[c]Mole/hr of sulfide + disulfide.

The data in Table III illustrate the cleavage of other organic sulfide according to the teaching of this invention.

TABLE III

| Run No. | Organic Sulfide | Press., Psig | Temp., °F | $H_2S/R_2S$ Mole/Hr | $R_2S/CS_2$ Mole/Hr | Conv., % | Yield %, n-RSH |
|---|---|---|---|---|---|---|---|
| 25 | Di-n-hexyl | 450 | 400 | 2.4/0.27 | 0.27/0.1 | 3.9 | 33.3 |
| 26 | Di-n-hexyl | 450 | 450 | 2.4/0.27 | 0.27/0.1 | 10.3 | 61.4 |
| 27 | Di-n-hexyl | 450 | 500 | 2.4/0.27 | 0.27/0.1 | 37.7 | 68.3 |
| 28 | Di-n-hexyl | 450 | 550 | 2.4/0.27 | 0.27/0.1 | 59.6 | 71.3 |
| 29 | Di-n-hexyl | 450 | 600 | 2.4/0.27 | 0.27/0.1 | 77.5 | 50.5 |
| 30 | Di-n-dodecyl | 450 | 500 | 1.31/0.15 | 0.15/0.59 | 27.6 | 38.8 |
| 31[a] | Di-n-dodecyl | 450 | 500 | 1.4/0.14 | 0.14/0.11 | 45.8 | 59.2 |
| 32[a] | Di-n-dodecyl | 180 | 500 | 1.4/0.14 | 0.14/0.11 | 44.7 | 59.3 |

[a]Feedstream contained 0.45 mole/hr benzene as a diluent.

The data in Table III illustrate the usefulness of the invention with regard to di-n-hexyl and di-n-dodecyl sulfides. Run 31 also illustrates the use of an inert diluent, benzene, in the feedstream.

I claim:

1. In the preparation of mercaptans by catalytic cleavage of organic sulfides with hydrogen sulfide in the presence of a sulfactive catalyst a method for increasing the total conversion of reactants to mercaptans comprises conducting the reaction in the presence of carbon disulfide in a mole ratio of at most about 50/1 of organic sulfide/carbon disulfide and at a temperature and pressure sufficient for carrying out the reaction.

2. The method of claim 1 wherein the carbon disulfide is added to the reaction mixture in a mole ratio in the range of about 0.1/1 to about 50/1 of organic sulfide/carbon disulfide.

3. The method of claim 2 wherein the organic sul-

TABLE II

| Run No.[a] | Organic Sulfide | Temp., °F | Conversion, %[f] Comparative[b] | Conversion, %[f] Inventive[c] | Yield, %, n-RSH[g] Comparative[b] | Yield, %, n-RSH[g] Inventive[c] |
|---|---|---|---|---|---|---|
| 1–2 | Dimethyl | 400 | 0 | 8.1 | — | 57.4 |
| 3–4 | Dimethyl | 450 | 1.1 | 26.9 | 100 | 82.5 |
| 5–6 | Dimethyl | 500 | 3.9 | 40.7 | 100 | 91.5 |
| 7–8 | Dimethyl | 550 | 13.9 | 41.7 | 100 | 88.5 |
| 9–10 | Di-n-butyl | 400 | 4.5 | 3.5 | 32.8 | 22.9 |
| 11–12 | Di-n-butyl | 450 | 10.8 | 16.3 | 56.2 | 56.6 |
| 13–14 | Di-n-butyl | 500 | 15.8 | 32.4 | 59.3 | 62.3 |
| 15–16 | Di-n-butyl | 550 | 16.0 | 58.8 | 54.9 | 63.1 |
| 17–18 | Di-n-butyl | 600 | 45.9 | 83.9 | 48.4 | 60.0 |
| 19–20 | Di-n-octyl[d] | 400 | 30.3[e] | 19.5[e] | 89.7 | 83.3 |
| 21–22 | Di-n-octyl[d] | 450 | 40.6[e] | 52.1[e] | 78.6 | 77.4 |
| 23–24 | Di-n-octyl[d] | 500 | 61.4[e] | 88.4[e] | 63.5 | 50.5 | a) Odd number - comparative runs; even numbers - inventive runs.
b) Comparative runs are without carbon disulfide.
c) Inventive runs are with carbon disulfide.
d) Mixture containing 43% di-n-octyl sulfide and 57% di-n-octyl disulfide.
e) Conversion based on consumed di-n-octyl sulfide and disulfide.
f) Conversion, % is defined as $$\frac{100(½ \text{ olefin} + ½n - \text{RSH} + ½ \text{ other RSH} + \text{other } R_2S + \text{other})(\text{expressed in moles})}{\text{the above} + \text{mole n-}R_2S}$$

g) Yield, %, n-RSH is defined as $$\frac{100(\text{moles n-RSH})}{(\text{n-RSH} + \text{other RSH} + 2 \text{ other } R_2S + 2 \text{ other} + \text{olefin})(\text{expressed in moles})}$$

The data in Table II show the enhanced conversion of organic sulfides to mercaptans resulting from use of carbon disulfide in the feedstream compared to prior art processes (comparative runs) employing no carbon disulfide. Only small differences were observed in yield of normal-mercaptans between inventive and comparative runs.

fides are represented by the formula R—S—R; wherein the R groups are independently selected from the group consisting of alkyl, cycloalkyl and aryl radicals and combination radicals such as alkylcycloalkyl, aralkyl, alkaryl and the like; wherein the R groups are selected such that the useful sulfides generally contain from 2 to about 40 or more carbon atoms per molecule with a preferable range of carbon atoms being from 2 to about 16.

4. The method of claim 3 wherein the reaction is carried out at temperatures ranging from about 177° to about 371° C and pressures are from about 100 to about 5000 psig.

5. The method of claim 4 wherein the organic sulfide is chosen from among the group comprising dimethyl sulfide, di-n-butyl sulfide and di-n-octyl sulfide.

* * * * *